(12) United States Patent
Oh et al.

(10) Patent No.: US 8,030,035 B2
(45) Date of Patent: Oct. 4, 2011

(54) D-PSICOSE PRODUCTION METHOD BY D-PSICOSE EPIMERASE

(75) Inventors: Deok-Kun Oh, Gwacheon (KR); Hye-Jung Kim, Seoul (KR); Yong-Joo Lee, Hwaseong (KR); Sang-Hoon Song, Bucheon (KR); Seung-Won Park, Yongin (KR); Jung-Hoon Kim, Seoul (KR); Seong-Bo Kim, Seoul (KR)

(73) Assignee: CJ Cheiljedang Corp. (KR)

( * ) Notice: Subject to any disclaimer, the term of this patent is extended or adjusted under 35 U.S.C. 154(b) by 946 days.

(21) Appl. No.: 11/916,182

(22) PCT Filed: May 30, 2006

(86) PCT No.: PCT/KR2006/002075
§ 371 (c)(1),
(2), (4) Date: Nov. 30, 2007

(87) PCT Pub. No.: WO2006/129954
PCT Pub. Date: Dec. 7, 2006

(65) Prior Publication Data
US 2010/0190225 A1   Jul. 29, 2010

(30) Foreign Application Priority Data
Jun. 1, 2005 (KR) ......................... 10-2005-0046559

(51) Int. Cl.
*C12P 19/24* (2006.01)
(52) U.S. Cl. ........................................... 435/94
(58) Field of Classification Search ........................ None
See application file for complete search history.

(56) References Cited

OTHER PUBLICATIONS

Wood et al. Database: PIR, Accession No. AB3141 (Jul. 2004).*
Goodner et al. Database: PIR, Accession No. B98147 (Jul. 2004).*
Ishida, Y., et al.; "Production of D-Tagatose 3-Epimerase of *Pseudomonas cichorii* ST-24 Using Recombinant *Escherichia coli*"; Journal of Fermentation and Bioengineering; vol. 84, No. 4; pp. 348-350; 1997.
Takeshita, K., et al.; "Mass Production of D-Psicose from D-Fructose by a Continuous Bioreactor System Using Immobilized D-Tagatose 3-Epimerase"; Journal of Bioscience and Bioengineering; vol. 90, No. 4; pp. 453-455; 2000.
Itoh, H., et al.; "Preparation of D-Psicose from D-Fructose by Immobilized D-Tagatose 3-Epimerase"; Journal of Fementation and Bioengineering; vol. 80, No. 1; pp. 101-103; 1995.
Kim, H., et al.; "Characterization of an *Agrobacterium tumefaciens* D-Psicose 3-Epimerase That Converts D-Fructose to D-Psicose"; Applied and Environmental Microbiology; vol. 72, No. 2; pp. 981-985; Feb. 2006.
NCBI GenBank Accession No. NP_535228, Dec. 14, 2001.
Matsuo, T., et al.; "D-Psicose, a rare sugar that provides no energy and additionally beneficial effects for clinical nutrition"; ICCN Poster Presentation, Asia Pacific J. Clin. Nutr.; 13:S127, 2004.
Matsuo, T., et al.; "Dietary D-psicose, a C-3 epimer of D-fructose, suppresses the activity of hepatic lipogenic inzymes in rats"; Asia Pacific J. Clin. Nutr.; vol. 10, No. 3; pp. 233-237; 2001.
European Search Report; Application No. EP 06768700.4; Date: May 21, 2008.
Wood, D.W., et al.; "The Genome of the Natural Genetic Engineer *Agrobacterium tumefaciens* C58"; Science; vol. 294; pp. 2317-2323; Dec. 2001.
Chinese Office Action with English Translation for Application No. 200680018899.3 dated May 26, 2010.
NCIB:NP_535228 Protein-D-tagatose 3-epimerase [*Agrobacterium tumefaciens* str.C58] Dec. 14, 2001.
Itoh, et al., Preparation of D-Psicose from D-Fructose by lmmobilzed D-Tagatose 3-Epimerase, Journal of Fermentation and Bioengineering, vol. 80, No. 1, 101-103, 1995.
Japanese Office Action for Application No. 2008-514546 dated Jul. 21, 2010.
Takeshita, et al., Mass Production of D-Psicose from D-Fructose by a Continuous Bioreactor System Using Immobilized D-Tagatose 3-Epimerase, Journal of Biosci Bioengineering, vol. 90, No. 4, 453-455, 2000.

* cited by examiner

*Primary Examiner* — Nashaat Nashed
(74) *Attorney, Agent, or Firm* — Cantor Colburn LLP

(57) ABSTRACT

Provided is a method of producing D-psicose using a D-psicose epimerase derived from *Agrobacterium tumefaciens*. Provided are a protein having an amino acid sequence of SEQ ID NO:1 and having a psicose 3-epimerase activity, a gene encoding the protein, a recombinant expression vector containing the gene, and a method of producing D-psicose by reacting the protein produced on a mass scale with D-fructose. The method of producing D-psicose is an environmentally friendly method using a new enzyme, in which an inexpensive substrate is used, and the activity of the enzyme can be retained for a prolonged time period. Thus, the method can be efficiently used for the mass production of D-psicose.

4 Claims, 2 Drawing Sheets

D-PSICOSE PRODUCTION METHOD BY D-PSICOSE EPIMERASE

CROSS-REFERENCE TO RELATED PATENT APPLICATION

This application is a 371 national stage application of International Application PCT/KR2006/002075, filed May 30, 2006, which claims priority to Korean Patent Application No. 10-2005-0046559, filed on Jun. 1, 2005, in the Korean Intellectual Property Office, the disclosure of which is incorporated herein in its entirety by reference.

BACKGROUND OF THE INVENTION

1. Field of the Invention

The present invention relates to a method of producing D-psicose using a D-psicose epimerase (hereinafter, referred to as psicose 3-epimerase) derived from *Agrobacterium tumefaciens*.

2. Description of the Related Art

In general, D-psicose is an epimer of D-fructose, and is very similar to D-fructose in the aspects of intensity and type of sweetness. However, unlike D-fructose, D-psicose is hardly metabolized during assimilation in the body, and has a low degree of caloric contribution. Thus, D-psicose can be used as an effective ingredient of diet foods. While sugar alcohols, which are widely used as a non-sugar sweetener, cause side effects such as diarrhea when more than a stipulated dose is ingested, D-psicose has no such side effects. Furthermore, D-psicose has a calorie value of nearly zero, as it is almost non-metabolizable in the human body, and has a function of reducing abdominal fats by suppressing the activity of lipogenic enzymes. Therefore, D-psicose can be used as a sweetener which is also helpful in weight reduction (See, for example, Matsuo, T., Y. Baba, M. Hashiguchi, K. Takeshita, K. Izumori and H. Suzuki, "Dietary D-psicose, a C-3 epimer of D-fructose, suppresses the activity of hepatic lipogenic enzymes in rats," *Asia Pac. J. Clin. Nutr.*, 10:233-237 (2001); and Matsuo, T. and K. Izumori, "D-Psicose, a rare sugar that provides no energy and additionally beneficial effects for clinical nutrition," *Asia Pac. J. Clin. Nutr.*, 13:S127 (2004)).

In this light, D-psicose is attracting great interest as a dietary sweetener, and there is an increasing demand in the food industry, for the development of a method of producing D-psicose efficiently. This is because D-psicose only exists in a very small amount in nature as an intermediate during the process of theriae treatment or glucose isomerization reaction, and cannot be chemically synthesized.

Therefore, in order to address such problems as described above, research is being conducted on methods of enzymatically producing D-psicose using D-fructose as a substrate.

However, there is a problem in the methods developed so far, that the production costs are high, owing to the low yield of D-psicose.

SUMMARY OF THE INVENTION

The inventors of the present invention made an attempt to select an enzyme which can produce D-psicose with a high yield using D-fructose as a substrate, from epimerase enzymes that are characterized not by function, but merely by base sequence or amino acid sequence, and demonstrated specific effects of the selected enzyme. The present invention provides a new method of producing D-psicose with a high yield using the selected enzyme.

According to an aspect of the present invention, there is provided a protein having an amino acid sequence of SEQ ID NO:1, and having an activity of psicose 3-epimerase.

According to another aspect of the present invention, there is provided a gene encoding the protein.

According to another aspect of the present invention, there is provided a recombinant expression vector containing the gene.

According to another aspect of the present invention, there is provided a method of producing D-psicose by reacting the above-described protein with D-fructose.

Hereinafter, the present invention will be described in detail.

It is understood that the technical terms and scientific terms used herein refer to the terms conventionally understood by those having ordinary skill in the art, unless stated otherwise.

Furthermore, descriptions on technical constitutions and mechanisms which are the same as conventionally known technical constitutions and mechanisms will not be repeated.

The present inventors investigated the characteristics of uncharacterized tagatose 3-epimerase derived from *Agrobacterium tumefaciens* by cloning a gene of tagatose 3-epimerase derived from *Agrobacterium tumefaciens* or a gene corresponding to the tagatose 3-epimerase, culturing a microorganism transformed with an expression vector containing the gene, and overexpressing tagatose 3-epimerase. As a result, it was found that tagatose 3-epimerase had higher specificity for psicose than for tagatose, and thus, it was demonstrated that the "known-to-be" tagatose 3-epimerase derived from *Agrobacterium tumefaciens* was actually psicose 3-epimerase. Thus, the present invention provides a method of producing D-psicose using the psicose 3-epimerase.

More specifically, in an attempt to obtain the gene of a known tagatose 3-epimerase useful for the present invention, bacterial strains known to produce the gene of the tagatose 3-epimerase were used, and the bacterial strains include *Thermotoga maritima, Streptomyces coelicolor, Mesorhizobium loti, Agrobacterium tumefaciens, Rhodopirellula baltica, Pirellula* sp., *Photorhabdus luminescens* subsp. *laumondii*, and *Sinorhizobium meliloti*. It was demonstrated for the first time by the present invention that only the enzyme (NP_535228; SEQ ID NO:1) expressed from a gene derived from the *Agrobacterium tumefaciens* ATCC33970 has an activity which can convert D-fructose to D-psicose.

In order to determine the characteristics of tagatose 3-epimerase, in the present invention, tagatose 3-epimerase genes were obtained in large amounts through a polymerase chain reaction (PCR) from bacterial strains containing tagatose 3-epimerase genes which were designated merely according to the DNA base sequence, not according to the results of characterization in the aspect of the enzymatic function. Then, the obtained tagatose 3-epimerase genes were inserted into appropriate expression vectors to produce recombinant vectors containing the tagatose 3-epimerase genes, and the recombinant vectors were transformed into appropriate microorganisms. The transformed microorganisms were cultured in fermentation media, and protein products of the tagatose 3-epimerase genes were overexpressed in the microorganisms. The protein products of the tagatose 3-epimerase genes were then isolated and purified for use.

The method of producing D-psicose of the present invention includes reacting psicose 3-epimerase (usually known as tagatose 3-epimerase) with fructose used as a substrate.

The psicose 3-epimerase produced by the method of the present invention may have an amino acid sequence which is not limited to the amino acid sequence of SEQ ID NO:1, but also includes the amino acid sequences resulting from substitution, insertion or deletion of some amino acid residues in the amino acid sequence of SEQ ID NO:1, provided that these modified amino acid sequences are capable of converting D-fructose to D-psicose.

In the method of the present invention, an expression vector that can be used to produce a recombinant expression vector may be any expression vector conventionally used in the genetic recombination technology, and may be, for example, pET-24a(+). The microorganism that can be transformed with the recombinant expression vector may be *E. coli* BL21 (DE3). However, the microorganism is not limited provided that it is any bacterial strain which is able to overexpress a desired gene, after being transformed with a recombinant expression vector containing the gene, and also able to produce an active protein as a result of the overexpression.

In more detail, the following processes of culturing a transformed microorganism and inducing overexpression of the protein of the present invention may be performed according to an exemplary embodiment of the present invention as described below. A cryogenically stored inoculum of *Escherichia coli* BL21(DE3) is inoculated in a 250-ml flask containing 50 ml of an LB medium, and the strain is cultured in a shaking incubator maintained at 37° C., until absorbance at 600 nm reaches 2.0. The cultured solution is added to a 7-L fermentor (Biotron Co., Ltd., Korea) containing 5 L of a fermentation medium composed of 10 g/L of glycerol, 1 g/L of peptone, 30 g/L of yeast extract, 0.14 g/L of potassium diphosphate and 1 g/L of sodium monophosphate, and the mixture is incubated in the fermentor until absorbance at 600 nm reaches 2.0. Then, 1 mM of ITPG is added to induce overexpression of the protein of the present invention. During the operation, the rate of stirring may be maintained at 500 rpm, the ventilation rate at 1.0 vvm, and the incubation temperature at 37° C., and such incubation conditions as described above are favorable for the mass production of psicose 3-epimerase.

In order to purify the protein produced by overexpression, the culture solution of the transformed bacterial strain is centrifuged at 6,000×g at 4° C. for 30 minutes, and then washed twice with 0.85% NaCl. Subsequently, the cells are added to a cytolytic buffer solution (50 mM $NaH_2PO_4$, 300 mM NaCl, pH 8.0) containing 1 mg/ml of lysozyme, and the cytolytic buffer solution containing the cells is left to stand in an ice bath for 30 minutes. The cells in the cytolytic buffer solution are disrupted by a French press at a pressure of 15,000 $lb/in^2$, and the disrupted cells are subjected to centrifugation at 13,000×g at 4° C. for 20 minutes and removed, while the supernatant is filtered through a filter paper with a pore diameter of 0.45 µm, and purified by fast protein chromatography (FPLC) under a cryogenic condition. The filtrate, which contains the protein of the present invention, is applied to a HisTrap HP column which has been equilibrated with a 50 mM phosphate buffer solution at pH 8.0 containing 300 mM of sodium chloride (NaCl) and 10 mM of imidazole. Subsequently, the HisTrap HP column is washed with the same phosphate buffer solution, and then the protein attached to the column is eluted with the same phosphate buffer solution containing imidazole at a gradient concentration from 10 mM to 200 mM, at a flow rate of 1 ml/min. The eluted fraction containing the protein of the present invention is added to a HiPrep 16/60 demineralized resin column which has been equilibrated with a 50 mM PIPES buffer solution at pH 7.5, and then, the protein is washed out at a rate of 6 ml/min. A solution of the protein thus collected is applied to a Sephacryl S-100 HR column which has been equilibrated with a 50 mM PIPES buffer solution at pH 7.5 containing 0.15 M sodium chloride, at a flow rate of 6.6 ml/min to elute the protein. The eluted protein is finally dialyzed in a 50 mM PIPES buffer solution.

The protein of the present invention obtained as described above is a psicose 3-epimerase, which is a monomer having a molecular weight of 32,600 Da. This psicose 3-epimerase is a metalloenzyme, the activation of which is regulated by metal ion.

According to another embodiment of the present invention, the reaction between the psicose 3-epimerase and D-fructose may be performed in the presence of a metal ion selected from the group consisting of manganese, magnesium, iron, cobalt and aluminum, at a concentration of 0.5 to 5 mM, for example, 1 mM, for the purpose of improving the production yield of D-psicose. When the concentration of the metal ion is less than 0.5 mM, the effect of improving the production yield is negligible, while when the concentration of the metal ion is greater than 5 mM, the improvement is less effective relative to the amount of excess.

The reaction between the psicose 3-epimerase and D-fructose may be performed using a substrate (i.e., D-fructose) concentration of 55 to 75% (w/w), at pH 7 to 8, and at a temperature of 55 to 65° C. When the concentration of the substrate which is D-fructose is in the range of 55 to 75% (w/w), the production yield of D-psicose is good, and the pH and temperature conditions of the above-mentioned ranges are optimal pH and temperature ranges for the psicose 3-epimerase activity.

According to another embodiment of the present invention, the reaction between the psicose 3-epimerase and D-fructose to produce D-psicose may be performed by immobilizing the psicose 3-epimerase on a carrier during the reaction, since psicose 3-epimerase immobilized on a carrier can maintain enzyme activity for a prolonged time period. The carrier useful for the current embodiment of the present invention may be any of the carriers known for their use in enzyme immobilization, and may be sodium alginate, for example. Sodium alginate is a natural colloidal polysaccharide which is abundant in the cell walls of algae, and contains β-D-mannuronic acid and α-L-guluronic acid residues, which are connected randomly by β-1,4 linkages. Thus, sodium alginate allows stable immobilization of the psicose 3-epimerase, and is advantageous for obtaining a high D-psicose yield. In order to obtain the maximum yield of D-psicose, sodium alginate may be used for the immobilization of the psicose 3-epimerase, at a concentration of 1.5 to 4.0% by weight, for example, 2.5% by weight. When sodium alginate is used as the carrier for immobilizing the psicose 3-epimerase, a solution of the psicose 3-epimerase may be added to an aqueous solution of sodium alginate with a one- or two-fold volume of the psicose 3-epimerase solution, and then the mixture is added dropwise to a 0.2 M calcium ion solution using a syringe pump and a vacuum pump, so that beads of a psicose 3-epimerase-sodium alginate complex are formed. These beads of the psicose 3-epimerase-sodium alginate complex may be directly used in the reaction with D-fructose.

The method of producing D-psicose according to embodiments of the present invention is environmentally friendly because an enzyme derived from a microorganism is used, requires a simple process for enzyme immobilization, and significantly increases the production yield of D-psicose, thereby reducing the production costs, while maximizing the effect of production.

The D-psicose thus produced can be usefully used as a dietary or pharmaceutical additive.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the present invention will be described in more detail with reference to specific Examples. These Examples are for illustrative purposes only and are not intended to limit the scope of the present invention.

Experimental Example

In the current Experimental Example, MALDI-TOF-MS was used for the measurement of the molecular weight of psicose 3-epimerase, and cinnamic acid was used as a matrix. The enzyme activity was measured by using D-fructose as a substrate. For the measurement of the enzyme activity, psicose 3-epimerase was allowed to react with D-fructose in a 50 mM PIPES buffer solution containing 1.0% of D-fructose, at pH 7.5 and at 50° C. for 20 minutes, and then the reaction solution was heated at 100° C. for 5 minutes to terminate the reaction. The PIPES buffer solution containing D-fructose was prepared by dissolving D-fructose in PIPES buffer solution at pH 7 to 8 to a concentration of 60 to 70% by weight, and the PIPES buffer solution containing D-fructose was continuously added to a bioreactor maintained at 40 to 60° C. For the purpose of easy comparison of the enzyme activity, one unit of psicose 3-epimerase is defined as the amount of the psicose 3-epimerase needed to produce 1 mole of D-psicose per one minute at pH 7.5 and at 50° C.

The concentrations of D-fructose, D-psicose, D-sorbose, D-tagatose, D-xylulose and D-ribulose were measured using a high pressure liquid chromatography system with a BP-100 calcium ion hydrocarbon column and an RI detector. The column was conditioned to allow a flow of distilled water at a rate of 0.5 ml/min at 80° C.

EXAMPLES

Physical Properties of psicose 3-epimerase

Example 1

Mass Production of psicose 3-epimerase

Figure 3:
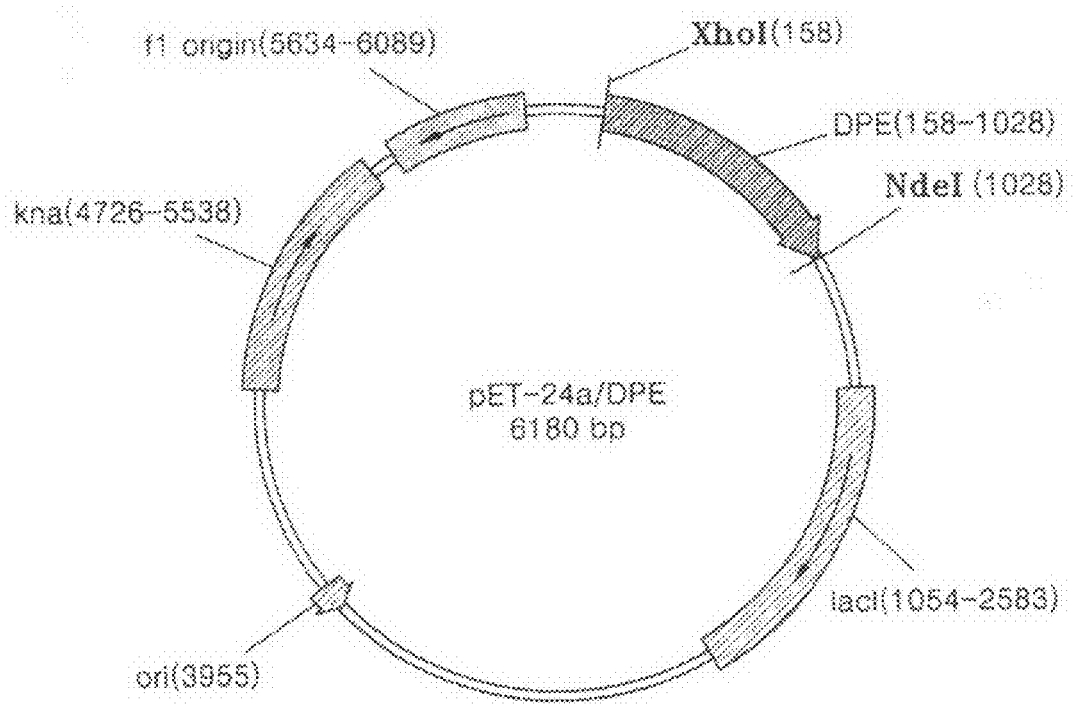
FIG. 3 is a cleavage map of a recombinant expression vector according to an embodiment of the present invention.

The gene of psicose 3-epimerase was obtained in a large amount by amplifying the DNA of *Agrobacterium tumefaciens* ATCC33970 by a polymerase chain reaction (PCR) using a primer designed based on the DNA base sequence of a gene that had been suggested as a tagatose 3-epimerase gene of *Agrobacterium tumefaciens* C58 but had not been functionally characterized. The obtained gene of psicose 3-epimerase was inserted in an expression vector, pET-24a(+) (Novagen, Inc.), by using restriction enzymes XhoI and NdeI to produce a recombinant expression vector pET-24a(+)/psicose 3-epimerase (See FIG. 3). This recombinant expression vector was transformed into *Escherichia coli* BL21(DE3) by a conventional transformation method. The transformed strain *E. coli* BL21(DE3) was cryogenically stored in liquefied nitrogen before being cultured for mass production.

Thereafter, an inoculum of the cryogenically stored *E. coli* BL21(DE3) strain was inoculated in a 250-ml flask containing 50 ml of LB medium, and was precultured in a shaking incubator at 37° C. until absorbance of the preculture solution at 600 nm reached 2.0. The preculture solution was added to a 7-L fermentor (Biotron Co., Ltd., KR) containing 5 L of a fermentation medium (10 g/L of glycerol, 1 g/L of peptone, 30 g/L of yeast extract, 0.14 g/L of potassium diphosphate and 1 g/L of sodium monophosphate), and was subjected to main culture. When absorbance of the main culture solution at 600 nm reached 2.0, 1 mM of ITPG was added to the main culture solution to induce mass production of the psicose 3-epimerase. During the culturing process, the rate of stirring was maintained at 500 rpm, the rate of ventilation at 1.0 vvm, and the incubation temperature at 37° C.

Example 2

Purification of psicose 3-epimerase

In order to perform characterization of the psicose 3-epimerase, the psicose 3-epimerase was purified using an affinity HisTrap HP column, a demineralized HiPrep 16/60 column, and a gel filtration Sephacryl S-100 HR column.

The molecular weight of the purified psicose 3-epimerase was measured, and it was found that the psicose 3-epimerase was a monomer having a molecular weight of 32,600 Da. The amino acid sequence of the psicose 3-epimerase was confirmed to be identical to the amino acid sequence of NCBI accession number NP_535228.

Example 3

Metal Specificity of psicose 3-epimerase

In order to investigate the effect of the addition of a metal ion, the enzyme activity of the psicose 3-epimerase was measured after treating the psicose 3-epimerase with EDTA, or after adding 1 mM each of the metal ions indicated in Table 1 below, to the psicose 3-epimerase. Reaction of the psicose 3-epimerase was performed in a 50 mM PIPES buffer solution containing 0.04 units/ml of the psicose 3-epimerase and 1.0% by weight of D-fructose at pH 7.5 and at 50° C. for 20 minutes, and then the reaction solution was heated at 100° C. for 5 minutes to terminate the reaction. Then, the enzyme activity of the psicose 3-epimerase was measured.

As a result, the psicose 3-epimerase was found to be a metalloenzyme, since manganese and cobalt ions enhanced the enzyme activity, while copper and zinc ions suppressed the enzyme activity as indicated below in Table 1.

TABLE 1

| Metal ion | Relative activity (%) |
|---|---|
| None | 100 |
| $Al^{3+}$ | 100 |

TABLE 1-continued

| Metal ion | Relative activity (%) |
|---|---|
| $Ba^{2+}$ | 95.6 |
| $Ca^{2+}$ | 64.4 |
| $Co^{2+}$ | 268 |
| $Cu^{2+}$ | 2.2 |
| $Fe^{3+}$ | 121 |
| $Fe^{2+}$ | 139 |
| $Mg^{2+}$ | 100 |
| $Mn^{2+}$ | 274 |
| $Mo^{2+}$ | 93.3 |
| $Zn^{2+}$ | 4.4 |
| EDTA | 20.0 |

Example 4

Substrate-Specificity of psicose 3-epimerase

Reaction of the psicose 3-epimerase was performed in a 50 mM PIPES buffer solution containing 0.04 units/ml of the psicose 3-epimerase and 10 mM each individually of the monosaccharides indicated in Table 2 below, at pH 7.5 and at 50° C. for 20 minutes, and then each of the reaction solutions were heated at 100° C. for 5 minutes to terminate the reaction. Then, the enzyme activity of the psicose 3-epimerase of each reaction solution was measured.

As a result, it was found that the psicose 3-epimerase had a higher affinity for D-psicose than that for D-tagatose. Thus, this psicose 3-epimerase was newly recognized as an enzyme capable of psicose epimerization, not a tagatose 3-epimerase.

TABLE 2

| | Relative activity (%) | |
|---|---|---|
| Monosaccharide | No metal ion added | $Mn^{2+}$ added |
| D-Psicose | 100 | 274 |
| D-Tagatose | 65.5 | 92.3 |
| D-Ribulose | 10.2 | 15.4 |
| D-Fructose | 37.9 | 139 |
| D-Sorbose | 0.8 | 1.7 |
| D-Xylulose | 5.8 | 12.4 |
| D-Fructose-6-phosphate | 0.0 | 0.0 |
| D-Ribulose-5-phosphate | 0.0 | 0.0 |

Example 5

Activity of psicose 3-epimerase According to pH and Temperature Changes

In Example 5, the psicose 3-epimerase was reacted with D-fructose at various pH values and temperatures, and the enzyme activities obtained at the various pH values and temperatures were compared. In order to investigate the pH effect, the reaction of the psicose 3-epimerase was performed in a 50 mM PIPES buffer solution containing 0.04 units of psicose 3-epimerase/ml and 1.0% of D-fructose at pH values ranging from 6.5 to 7.5, and the same reaction was performed in a 50 mM EPPS buffer solution containing 0.04 units of psicose 3-epimerase/ml and 1.0% of D-fructose at pH values ranging from 7.5 to 8.5. Here, the respective reactions were performed at 50° C. when metal ions were not added, and at 60° C. when Mn ions were added, respectively for 20 minutes. Then, the reactions were terminated by heating the reaction solutions at 100° C. for 5 minutes, and the enzyme activities were measured. The results are illustrated in FIG. 1A.

In order to investigate the temperature effect, the reaction was performed in a 50 mM PIPES buffer solution containing 0.04 units of psicose 3-epimerase/ml and 1.0% of D-fructose at temperatures ranging from 30° C. to 70° C. for 20 minutes, at pH 7.5 when metal ions were not added, and at pH 7.0 when Mn ions were added. The reactions were terminated by heating the reaction solution at 100° C. for 5 minutes, and the enzyme activities were measured. The results are illustrated in FIG. 1B.

As a result, the optimal pH and temperature for the psicose 3-epimerase when metal ions were not added was found to be 7.5 and 50° C., respectively. The optimal pH and temperature for the psicose 3-epimerase when $Mn^{2+}$ ions were added was 7.0 and 60° C., respectively.

Figure 1:
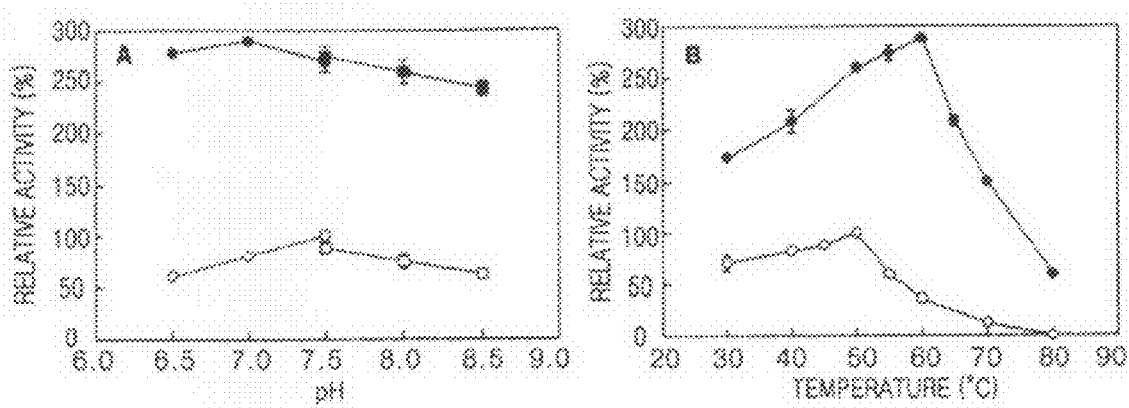
FIG. 1A is a graph showing the activity of a psicose 3-epimerase according to an embodiment of the present invention against reaction pH.
FIG. 1B is a graph showing the activity of a psicose 3-epimerase according to an embodiment of the present invention against reaction temperature.

FIG. 1A is a graph showing the activity of a psicose 3-epimerase according to an embodiment of the present invention against reaction pH. Referring to FIG. 1A, ○ indicates the result obtained in a PIPES buffer solution containing no metal ions; ● indicates the result obtained in a PIPES buffer solution containing $Mn^{2+}$ ions; □ indicates the result obtained in an EPPS buffer solution containing no metal ions; and ■ indicates the result obtained in an EPPS buffer solution containing $Mn^{2+}$ ions.

FIG. 1B is a graph showing the activity of a psicose 3-epimerase according to an embodiment of the present invention against reaction temperature. Referring to FIG. 1B, ○ indicates the result obtained in the absence of metal ions; and ● indicates the result obtained in the presence of 1 mM of $Mn^{2+}$ ions.

Example 6

Equilibrium Between D-psicose and D-fructose Achieved by psicose 3-epimerase

In Example 6, the reaction of the psicose 3-epimerase was performed in a 50 mM PIPES buffer solution containing 0.04 units of psicose 3-epimerase/ml, 1 mM of $Mn^{2+}$ ions, and 0.1% of D-psicose and D-fructose together, at pH 7.0 and at temperatures ranging from 30° C. to 60° C. for 24 hours to allow the reaction to proceed sufficiently, in order to determine the equilibrium between D-psicose and D-fructose. Then, the reactions were terminated by heating the reaction solution at 100° C. for 5 minutes, and the enzyme activity was measured.

Figure 2:
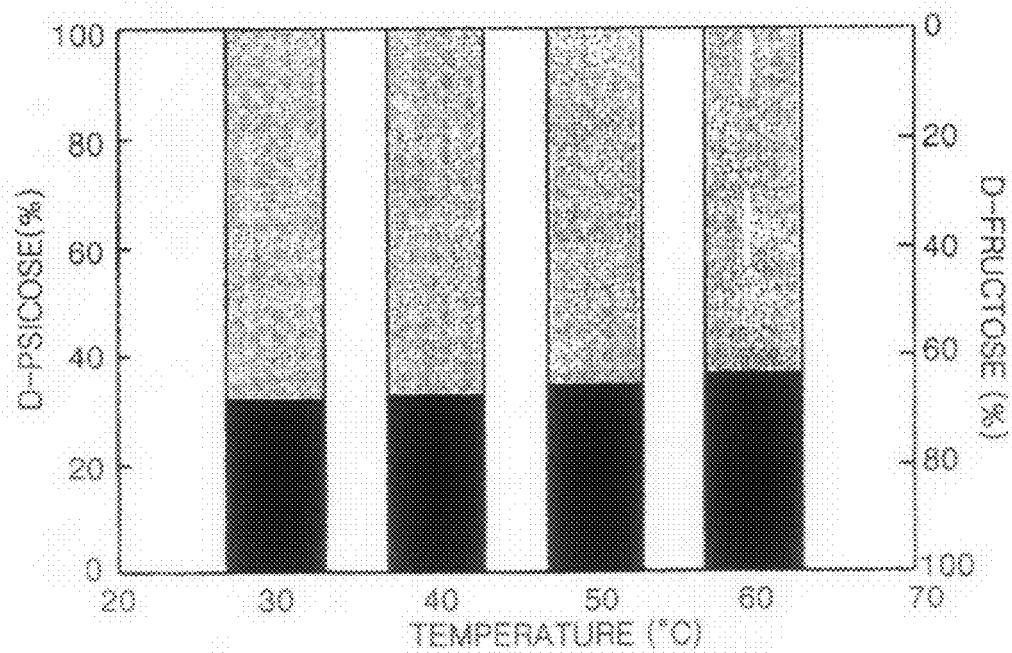
FIG. 2 is a graph showing the equilibrium ratios between D-psicose (■) and D-fructose (□) obtained when the psicose 3-epimerase according to an embodiment of the present invention is reacted with D-fructose at temperatures ranging from 30° C to 60° C.

FIG. 2 is a graph showing the equilibrium ratio of D-psicose (■) and D-fructose (□) achieved after the reaction of the psicose 3-epimerase according to an embodiment of the present invention with D-fructose at temperatures ranging from 30° C. to 60° C.

As a result, the reaction was started with 5 initial ratios of D-psicose to D-fructose, of 0:100, 25:75, 50:50, 75:25, and 100:0, and the final ratios of D-psicose to D-fructose were determined after 24 hours of the reaction, as shown in FIG. 2. Referring to FIG. 2, the ratio of D-psicose to D-fructose was 32:68 at 30° C., while the same ratio was 37:63 at 60° C. These results are approximately 20% superior to the yield achievable by conventional methods of producing D-psicose.

Example 7

D-psicose Production by psicose 3-epimerase

In order to produce D-psicose at high concentrations, the reaction was performed in a 50 mM PIPES buffer solution containing 14 units of psicose 3-epimerase/ml, 1 mM of $Mn^{2+}$ ions, and 700 g/L of D-fructose, at pH 7.0 and at 60° C. for various reaction times. Then, the reaction was terminated by heating the reaction solution at 100° C. for 5 minutes, and the enzyme activity was measured. The D-psicose production rates according to the reaction time are shown in Table 3 below.

TABLE 3

| Reaction time (min) | D-Psicose (g/L) |
|---|---|
| 0 | 0 |
| 10 | 93 |
| 30 | 155 |
| 60 | 180 |
| 120 | 211 |
| 180 | 210 |
| 240 | 210 |
| 300 | 209 |

As a result, 211 g/L of D-psicose was produced using a reaction time of 120 minutes, and this production rate corresponds to a D-psicose conversion yield of 30.2%.

Example 8

Production of D-psicose by Enzyme Immobilization

In order to investigate the efficiency of the method of producing D-psicose, the psicose 3-epimerase was immobilized during the reaction, and the production yields when the psicose 3-epimerase was not immobilized during the reaction and when the psicose 3-epimerase was immobilized during the reaction were compared.

For the psicose 3-epimerase immobilized on a carrier, beads of psicose 3-epimerase-sodium alginate complex were used, which were produced by adding a solution of the psicose 3-epimerase to a 2.5% sodium alginate solution having a volume 1.5 times the volume of the psicose 3-epimerase solution, and adding this mixture to a 0.2 M calcium ion solution with a syringe pump and a vacuum pump.

The reaction was performed in the same manner as in Example 7, except that immobilized psicose 3-epimerase was used. The amount of the psicose 3-epimerase used in the reaction was 140 units per 10 ml, and the D-psicose production rates were measured. The results are shown in Table 4 below.

TABLE 4

| Reaction time (min) | D-psicose (g/L) |
|---|---|
| 0 | 0 |
| 30 | 103 |
| 60 | 172 |
| 120 | 198 |
| 180 | 220 |
| 240 | 235 |
| 300 | 242 |
| 360 | 245 |

The free psicose 3-epimerase of Example 7 resulted in a maximum conversion rate of 211 g/L using a reaction time of 120 minutes. However, in the case of the immobilized psicose 3-epimerase of the current Example, the production speed was lower than that of the free psicose 3-epimerase, but the thermal stability of the immobilized psicose 3-epimerase was superior, and the concentration of D-psicose increased over time. Thus, the D-psicose production rate was 245 g/L after a reaction time of 360 minutes, and this production rate corresponded to a conversion yield of 35%.

Example 9

Production Yield of D-psicose in Bioreactor

The following reaction was performed in a bioreactor to verify the production yield of the immobilized psicose 3-epimerase of Example 8.

First, the immobilized psicose 3-epimerase and D-fructose were prepared in the same manner as in Example 8, D-fructose was added to the immobilized psicose 3-epimerase, and the mixture was then adjusted to a volume of 100 ml. Subsequently, a bioreactor (Pharmacia Biotechnologies, Inc., XK26, UK) having a height of 100 cm and a diameter of 26 cm was filled with the mixture of the immobilized psicose 3-epimerase and D-fructose, and the reaction was performed at a flow rate of 10 ml/h and at 60° C. The amount of the psicose 3-epimerase used was 500 units, and the concentration of D-fructose used was restricted to 600 g/L, due to the problem of precipitation of excess D-fructose during a long term operation. The results are shown in Table 5 below.

TABLE 5

| | Elapsed time (days) | | | | | | | | | | |
|---|---|---|---|---|---|---|---|---|---|---|---|
| | 0.5 | 1 | 1.5 | 2 | 3 | 5 | 10 | 15 | 20 | 25 | 30 |
| D-psicose production rate (g/L) | 55 | 180 | 210 | 211 | 210 | 209 | 212 | 211 | 211 | 211 | 212 |

As a result, the reaction between the psicose 3-epimerase and D-fructose was stable over the whole period of experiment of 30 days, and the productivity was 21 g/L/h, the conversion rate from D-fructose to D-psicose was 35%, while the production rate was 210 g/L. The yield is an excellent yield value in mass production of sugars.

Thus, the present invention can provide a D-psicose production system using a bioreactor which is capable of mass production of an industrial scale.

As described above, the method of producing D-psicose according to embodiments of the present invention is environmentally friendly because an enzyme derived from a microorganism is used, requires a simple process for enzyme immobilization, uses a substrate which is cheaper than that used in a conventional method, and significantly increases the production yield of D-psicose, thereby reducing the production costs, while maximizing the effect of production.

The D-psicose thus produced can be usefully used as a dietary or pharmaceutical additive.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of producing D-psicose comprising
contacting *Agrobacterium tumefaciens* tagatose 3-epimerase with D-fructose under conditions such that D-psicose is produced,
wherein the reaction is performed between pH 7 and 8 and at a temperature of between 55 and 65° C.

2. The method of claim 1, wherein the reaction is performed in the presence of a metal ion selected from the group consisting of manganese, magnesium, iron, cobalt and aluminum.

3. The method of claim 1, wherein the concentration of D-fructose used in the reaction is 55 to 75% (w/w).

4. The method of claim 1, wherein the *Agrobacterium tumefaciens* tagatose 3-epimerase is immobilized on a carrier.

* * * * *

SEQUENCE LISTING

<160> NUMBER OF SEQ ID NOS: 1

<210> SEQ ID NO 1
<211> LENGTH: 295
<212> TYPE: PRT
<213> ORGANISM: Agrobacterium tumefaciens

<400> SEQUENCE: 1

```
Met Lys His Gly Ile Tyr Tyr Ser Tyr Trp Glu His Glu Trp Ser Ala
 1               5                  10                  15

Lys Phe Gly Pro Tyr Ile Glu Lys Val Ala Lys Leu Gly Phe Asp Ile
                20                  25                  30

Ile Glu Val Ala Ala His His Ile Asn Glu Tyr Ser Asp Ala Glu Leu
            35                  40                  45

Ala Thr Ile Arg Lys Ser Ala Lys Asp Asn Gly Ile Ile Leu Thr Ala
        50                  55                  60

Gly Ile Gly Pro Ser Lys Thr Lys Asn Leu Ser Ser Glu Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Tyr Ala Arg
        115                 120                 125

Gly Val Glu Gly Ile Asn Gly Ile Ala Asp Phe Ala Asn Asp Leu Gly
    130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Ser Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
        275                 280                 285

Gly Leu Glu Asp Pro Ala Ala
    290                 295
```